United States Patent
Narayanan et al.

(10) Patent No.: US 6,200,326 B1
(45) Date of Patent: Mar. 13, 2001

(54) METHOD AND APPARATUS FOR HAIR REMOVAL USING ULTRASONIC ENERGY

(76) Inventors: Krishna Narayanan, 38 Easton Rd.; Marc D. Liang, 618 Whispering Pines La., both of Pittsburgh, PA (US) 15238

( * ) Notice: Subject to any disclaimer, the term of this patent is extended or adjusted under 35 U.S.C. 154(b) by 0 days.

(21) Appl. No.: 09/301,093

(22) Filed: Apr. 28, 1999

(51) Int. Cl.$^7$ .................................................. A61B 17/50
(52) U.S. Cl. ............................................................ 606/133
(58) Field of Search .............................. 606/36, 133, 131, 606/211, 43, 44; 604/22

(56) References Cited

U.S. PATENT DOCUMENTS

| | | | |
|---|---|---|---|
| 2,238,344 | | 4/1941 | Schuler et al. . |
| 3,054,405 | | 9/1962 | Tapper . |
| 3,315,678 | | 4/1967 | Donelson . |
| 3,589,363 | * | 6/1971 | Banko ................................... 604/22 |
| 4,016,882 | * | 4/1977 | Broadwing et al. ................. 606/169 |
| 4,598,709 | * | 7/1986 | Smith et al. ......................... 606/133 |
| 4,750,902 | * | 6/1988 | Wuchinich et al. ................... 604/22 |
| 4,908,015 | * | 3/1990 | Anis ...................................... 604/22 |
| 4,920,954 | | 5/1990 | Alliger et al. . |
| 4,940,466 | * | 7/1990 | Paduano et al. ....................... 606/36 |
| 5,012,797 | | 5/1991 | Liang et al. . |
| 5,112,300 | * | 5/1992 | Ureche .................................. 604/22 |
| 5,160,317 | * | 11/1992 | Costin .................................. 604/22 |
| 5,249,121 | * | 9/1993 | Baum et al. ............................ 606/1 |
| 5,279,547 | * | 1/1994 | Costin .................................. 604/22 |
| 5,879,314 | * | 3/1999 | Peterson et al. ........................ 601/2 |

FOREIGN PATENT DOCUMENTS

| | | | |
|---|---|---|---|
| 0736308 | 10/1996 | (EP) . | |
| 9107138 | * 5/1991 | (WO) .................................... 606/44 |

OTHER PUBLICATIONS

Richards. R. N., "Electrolysis: Observations from 13 Years and 140,000 Hours of Experience," Journal of the American Academy of Dermatology, vol. 33 No. 4, Oct. 1995, pp. 662–666.

Focus Surgery, Inc., "Focus Surgery," www.focus–surgery.com, 1997, pp. tech.html, sona.html, may14.htm, 14.htm 152.htm.

McElwee, K.J., "Hair Biology," www.keratin.com, 1999, pp. aa/aa0001.shtml, aa/aa002.shtml.

* cited by examiner

*Primary Examiner*—Gene Mancene
*Assistant Examiner*—Eduardo C. Robert
(74) *Attorney, Agent, or Firm*—Webb Ziesenheim Logsdon Orkin & Hanson, P.C.

(57) ABSTRACT

A new method and apparatus for the long-term removal of hair are provided. Ultrasonic energy is transmitted to a needle passed through the skin into an individual hair follicle. The resulting cavitation of the area surrounding the hair follicle causes the hair follicle to be disrupted. The process is repeated for individual hair follicles over the selected region of the body.

6 Claims, 2 Drawing Sheets

METHOD AND APPARATUS FOR HAIR
REMOVAL USING ULTRASONIC ENERGY

BACKGROUND OF THE INVENTION

1. Field of the Invention

The present invention generally relates to hair removal, and in particular the invention relates to the use of ultrasonic energy to disrupt hair follicles to remove hairs and to prevent their regrowth.

2. Description of the Prior Art

Removal of unwanted hair from different parts of the body is a well established modality in cosmetic surgery practice as well as in cosmetology. It is performed by physicians and aestheticians. Methods currently used to perform this procedure include electrolysis, laser energy, non-laser pulsed light, tweezing, waxing and chemical depilation.

Electrolysis is the removal of unwanted hair by means of a needle inserted into the hair follicle, through which an electrical current or radio energy is passed.

The short wave or radio energy method of electrolysis, also known as the thermolysis or diathermy method, uses high frequency radio energy, which sets up a rapid oscillation or vibration in the cells of the follicle, producing heat. The resulting heat cauterizes the hair tissue. A few seconds are required to heat each hair; in high-speed "flash" thermolysis the current is applied for only a fraction of a second. In the galvanic method, the direct current passed through the needle produces sodium hydroxide in the follicle, which chemically acts to destroy the hair tissue. A minute or more is required for treatment of each hair follicle.

The blend method combines both the short wave and galvanic modalities and, with the oscillation of the high frequency radio energy, the sodium hydroxide produced in the follicle is heated and destroys the hair tissue. These methods may result in some discomfort. They are claimed to provide lasting results.

The laser energy method involves the use of a laser, which is pulsed or turned on for only a fraction of a second. The laser works by selectively targeting the melanin pigment inside the hair follicle. The duration of the pulses is adjusted so that the energy will be absorbed by the hair follicle and will disable it, but will not result in the transfer of excess heat to the surrounding skin. This method may employ a wide beam, so that many hairs can be treated at once.

In some laser processes a thin coat of a clear gel is applied to the skin before the laser pulses are applied. Other laser processes employ waxing before laser pulse application. The use of anesthesia may not be necessary. Most individuals experience a slight stinging sensation as the laser pulses are applied. Some parts of the body do tend to be more sensitive than others, and sometimes redness or swelling will occur for a few hours afterwards. Burning or scarring can result if the treatments are administered improperly. Hyperpigmentation or hypopigmentation may also result.

Laser methods produce lasting, but not permanent, results. They are among the most expensive methods of hair removal. Hair growth may be inhibited to some extent. A number of sessions may be required, depending on the part of the body being treated. The process removes visible hair and disables hair in the active or anagen phase. Follicles in the resting or telogen phase are not affected; additional sessions are required to treat these hairs as they enter the active phase. Treatment may prolong the telogen phase. The process is of limited effectiveness on light hair.

A variation of these methods makes use of a carbon lotion applied before exposure to laser light. Carbon particles in the lotion, rather than melanin, absorb the laser light.

The non-laser pulsed light method uses intense, pulsed light. In the dermis, light energy is converted to heat and absorbed by hair pigment to destroy the hair structures and impair hair regrowth. The skin is protected from thermal injury as it is allowed to cool between pulses of light while a high heat level is maintained in the hair follicle.

Treatment parameters can be customized to the particular body area, hair depth, hair color and skin type of the individual patient. The process is claimed to be effective at skin depths or 1 to 2 mm, greater than the depths at which laser processes can be used. The method has a much larger spot size than traditional laser technology, so it can cover the treatment area faster and in fewer sessions.

The non-laser pulsed light method offers long-lasting, but not permanent, results.

Waxing is a process in which a warm wax mixture (or, alternatively, a sugar mixture) is applied to the area to be treated, and spread in the same direction as hair growth. A cloth is then patted down onto the area, and removed quickly, after a few seconds, in the direction opposite to hair growth. The process is repeated until all the hair is removed. The area will remain free of hair for three to six weeks.

However, follicle and root are stressed and deformed in this process. As a result, the follicle can become distorted or curved, and an ingrown hair may result.

Tweezing or plucking is a process in which individual hairs are physically removed. It requires a great deal of time to treat even small areas, and can be painful. It is not recommended for large or more sensitive areas. As is the case with waxing, the process stresses the follicle and root. Distortion or curving of the follicle and an ingrown hair may result.

A variation on the tweezing method employs an epilator, a device using rotating disks to grab the hair and pluck it out. Hairs to be removed must be of a length sufficient for the epilator to grab them firmly. The process is less time-consuming than tweezing, but the pain level may be the same.

Another variation uses tweezing in conjunction with electrical current. Hair is not an electrical conductor, so it does not transmit current from tweezers to a hair bulb. Since the follicle is not exposed to electrical current, hair removal is not permanent.

Chemical depilation is carried out by applying a depilatory cream and allowing sufficient time for the cream to act on the hair. The cream and hair are removed, razor fashion, with a spatula and the skin is rinsed and wiped to remove any remaining material. The method works best on large areas. It is temporary, removing hair for a slightly longer period of time than shaving. It may cause problems to users with sensitive skin.

Ultrasonic tools are widely used in surgical practice for applications other than the removal of hair. They are used in neurosurgery, cataract removal, and the removal of tissue. Most of the instruments used in these applications have a distal tip which undergoes longitudinal or transverse vibrations when subjected to ultrasonic energy. The distal end may be either solid or have a linear aspirating passage to facilitate the removal of unwanted tissue debris.

Typically, the ultrasonic devices operate at 23 kHz, 37 kHz, or 40 kHz. Typical power output ranges between 20 and 100 watts.

Consequently, a need remains for a permanent method of hair removal in which burns and scarring are avoided, and which targets the hair follicle while not resulting in damage to other anatomic structures.

SUMMARY OF THE INVENTION

In order to meet this need, I have developed a method and apparatus for the use of ultrasonic energy for long term hair removal. The apparatus includes an ultrasonic generator with a switch control, a handpiece, and a needle. The device is modified to provide a 20 kHz to 55 kHz output. Typically the output of the device is in the range of 30 watts to 80 watts. In use, a selected hair is targeted. The needle is passed through the skin into the area of the follicle. The generation of ultrasonic energy is begun, and this energy is transmitted to the needle, causing it to vibrate. This results in cavitation of the area surrounding the hair follicle, causing the hair follicle to be disrupted. The process is then repeated for individual hair follicles over the selected region of the body.

The handpiece contains a passageway dispensing an irrigating fluid to cool the needle. The irrigating fluid is dispensed at the end of the handpiece nearer the needle, and is preferably delivered as a mist.

A hollow or solid needle can be used. The skin can be anesthetized, if needed, with local anesthetic such as xylocaine. Alternatively, EMLA (eutectic mixture of local anesthetic) cream can be topically applied to relieve the patient of the pain resulting from the needle prick.

DETAILED DESCRIPTION OF THE PREFERRED EMBODIMENTS

Figure 1:
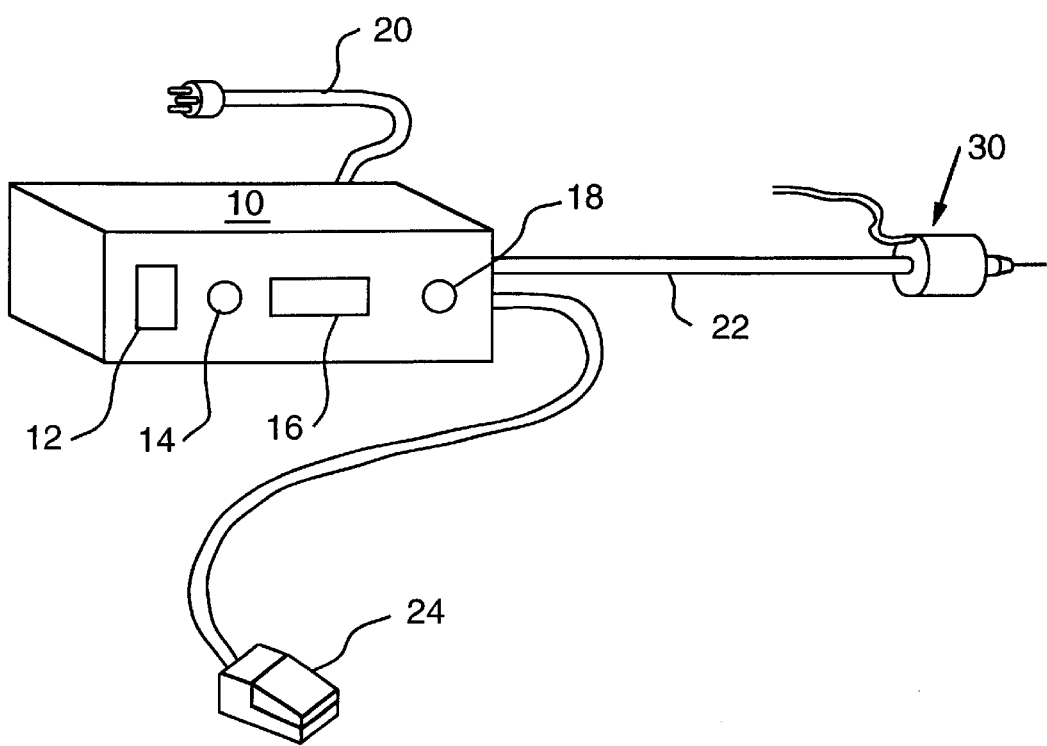
FIG. 1 shows the components of the apparatus, including the ultrasonic generator and handpiece.
Figure 2:
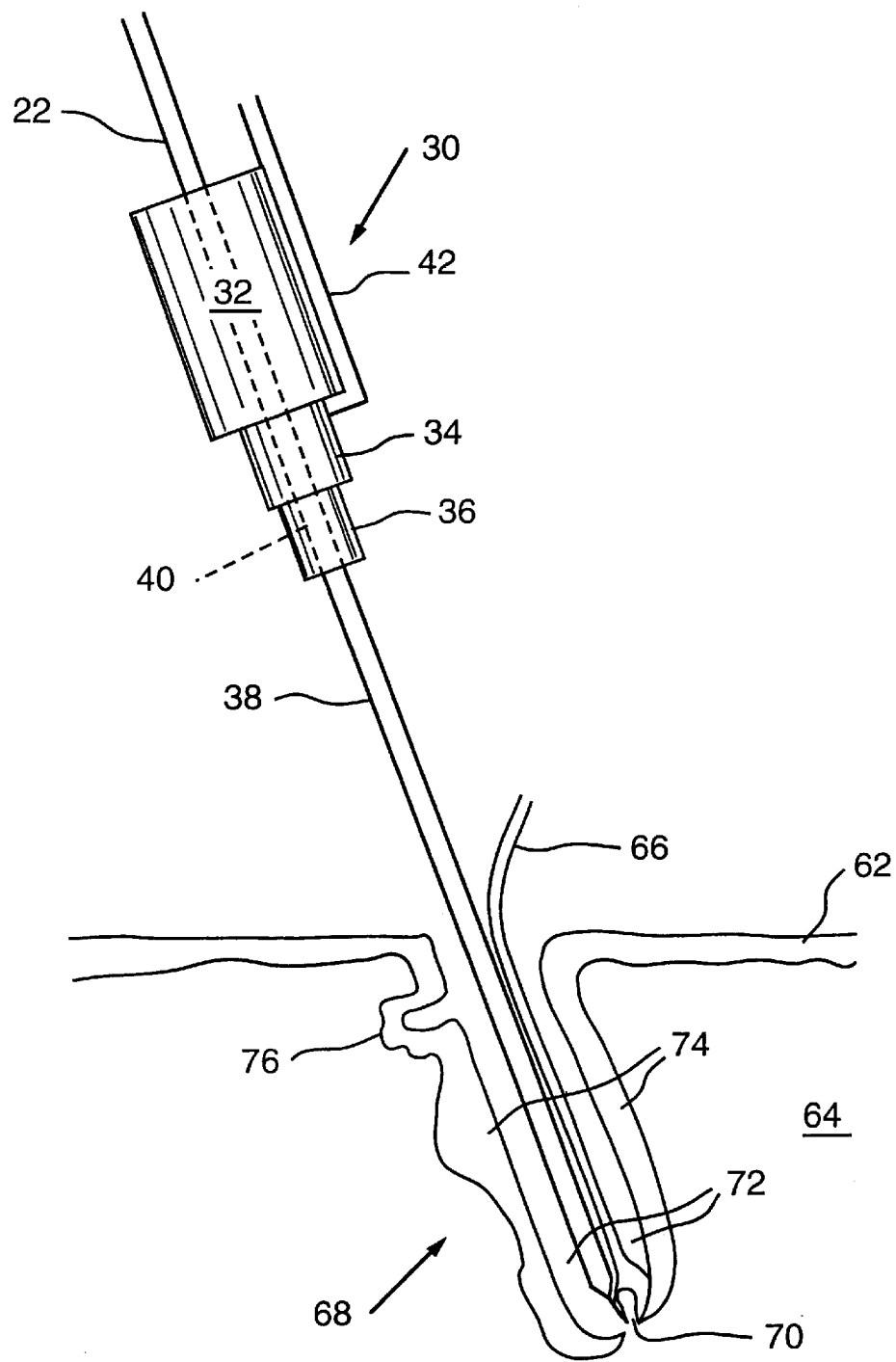
FIG. 2 is a side elevation of an ultrasonic surgical tool and a fragmentary cross-section of a region of skin containing a hair follicle.

The ultrasonic generator 10 has an on/off switch 12, a power setting control knob 14, a power meter 16, and a frequency selector 18. The generator also has a power line 20 for connection to a conventional 120 volt outlet, and a connection line 22 which extends from the generator to a handpiece 30. Switch control 24 enables the generator to be switched on and off by foot or in another manner when the operator's hands are occupied.

The handpiece 30 contains a transducer 32 that converts high frequency alternating current into high frequency alternating current into high frequency vibrations. The handpiece 30 is of a size and weight allowing comfortable handling by the operator. The handpiece may be a magnetostrictive device, in which magnetic energy is converted to mechanical energy, or it may be a piezoelectric device, in which an applied electrical field is converted to mechanical energy.

The transducer provides a 20 kHz to 55 kHz output to a solid or a hollow titanium stainless steel or aluminum needle. The power output is preferentially in the range of 20 to 100 watts. The vibrations are transmitted by a vibrating transmitting rod 40 to the needle 38. Titanium is a preferred material for the transmitting rod and the needle, as it is chemically inert, sufficiently hard to resist cavitation erosion, relatively non lossy to sound waves, suitable in terms of stress/strain characteristics and has a low modulus of elasticity. A solid or hollow needle tip with a diameter in the range from about 0.002 mm to 0.020 mm can be used. Disposable needles of this description are available.

A manifold 34 is provided for receiving cooling liquid from a conduit 42. The cooling liquid is delivered, as a drip or as a mist, from the conduit 42 through the manifold 34 and in the annular space between the rod 40 and the pipe 36 to the region of the oscillating tip 38. The cooling liquid is aqueous saline solution.

The hair follicle 68 is a small sac, located below the epidermis 62, and within the subcutaneous tissue 64, containing a sebaceous gland 76 and the structures for hair growth. Inner root sheath 72 and outer root sheath layers 74 enclose the dermal papilla 70. The dermal papilla directs the generation of the hair follicle and the hair fiber 66. The hair fiber is produced from cells made in the center of the hair follicle. As the hair fiber cells are formed, they are forced upwards towards the skin surface. The shape of the cells changes; they are squeezed together into layers, become keratinized, harden and die.

If the dermal papilla is removed, hair growth stops. However, the lower third of the hair follicle can supply new cells for the regeneration of the dermal papilla, if it remains intact. If more than the lower third of the follicle is removed, the regeneration of the dermal papilla does not occur and the follicle is permanently destroyed.

There are three phases of hair development. Anagen hair is hair in the active growth phase. Catagen hair is hair in an intermediate phase between growth and resting phases. Telogen hair is hair in a resting phase before shedding. Anagen follicles constitute 70% to 80% of the hair follicles on the scalp, but may account for as little as 20% to 50% of the hair follicles elsewhere on the body.

The present invention involves the treatment of hair follicles in the anagen phase. The needle is inserted into the follicle between the inner root sheath 72 and the hair fiber 66. The needle is inserted to the depth of the dermal papilla. Care is exercised not to puncture the outer root sheath. The pain resulting from needle prick can be relieved by the topical application of EMLA cream before treatment begins or by infiltrating the area with local anesthetic.

After the needle is inserted, alternating electrical current is applied to the transducer to set the needle tip in vibratory motion. The intense cavitation results in the disruption of the follicle. The needle is then removed from the follicle, and the process is then repeated for other hairs in the area to be treated. The skin is irrigated as necessary for cooling.

Only the follicle and associated structures are targeted by cavitation and not by heat as in conventional electrolysis, so the effect on adjacent tissues is minimized. This reduces the possibility of scarring. The follicle is completely disrupted, so the result is permanent. Post-procedure discomfort to the patient is minimal. There is no blood loss resulting from this procedure.

Although the invention has been described with particularity above, with reference to specific materials and methods, the invention is to be considered to be limited only insofar as is set forth in the accompanying claims.

We claim:

1. A method for disrupting a plurality of hair follicles, comprising:

passing a needle through the skin into the area of one of the plurality of hair follicles of a hair; and generating ultrasonic vibrations in the needle, resulting in disruption of the one of the plurality of hair follicles, wherein said passing step and said generating step are repeated for others of the plurality of hair follicles in the area to be treated to accomplish disruption of the plurality of hair follicles.

2. The method of claim 1 wherein the ultrasonic vibrations are within the frequency range from about 23 kHz to about 50 kHz.

3. The method of claim 1 wherein the needle is composed of titanium.

4. The method of claim 1 wherein the needle is hollow.

5. The method of claim 4 further comprising injecting the skin with a local anesthetic.

6. The method of claim 1 further comprising applying topical anesthetic to the skin.

\* \* \* \* \*